(12) United States Patent
Witteler et al.

(10) Patent No.: US 7,122,618 B2
(45) Date of Patent: Oct. 17, 2006

(54) QUATERNARY POLYAMIDOAMINES, THE PRODUCTION THEREOF, CORRESPONDING AGENTS AND THE USE THEREOF

(75) Inventors: Helmut Witteler, Wachenheim (DE); Axel Sanner, Frankenthal (DE); John-Bryan Speakman, Bobenheim (DE); Christian Drohmann, Schifferstadt (DE); Mathias Hahn, Wilhelmshorst (DE); Werner Jaeger, Kleinmachnow (DE)

(73) Assignee: Fraunhofer Gesellschaft zur Foerderung der Angewandteri Forschung E.V., Munich (DE)

( * ) Notice: Subject to any disclaimer, the term of this patent is extended or adjusted under 35 U.S.C. 154(b) by 110 days.

(21) Appl. No.: 10/485,262

(22) PCT Filed: Aug. 12, 2002

(86) PCT No.: PCT/EP02/09026

§ 371 (c)(1),
(2), (4) Date: Jun. 30, 2004

(87) PCT Pub. No.: WO03/014192

PCT Pub. Date: Feb. 20, 2003

(65) Prior Publication Data

US 2004/0234493 A1  Nov. 25, 2004

(30) Foreign Application Priority Data

Aug. 10, 2001 (DE) .................... 101 39 452

(51) Int. Cl.
| C08G 69/26 | (2006.01) |
| A61K 7/00 | (2006.01) |
| A61K 31/74 | (2006.01) |
| A61K 47/48 | (2006.01) |

(52) U.S. Cl. .................. 528/332; 528/310; 528/322; 528/335; 528/336; 525/451; 525/539; 424/78.17

(58) Field of Classification Search ............. 525/451, 525/539, 332; 528/363, 310, 322; 424/78.17
See application file for complete search history.

(56) References Cited

U.S. PATENT DOCUMENTS

| 4,240,450 A | 12/1980 | Grollier et al. |
| 4,247,476 A | 1/1981 | Haase et al. |
| 4,304,563 A | 12/1981 | Grollier et al. |
| 4,349,532 A | 9/1982 | Vanlerberghe et al. |
| 4,371,517 A | 2/1983 | Vanlerberghe et al. |
| 4,395,541 A | 7/1983 | Lang et al. |
| 4,436,524 A | 3/1984 | Valenti |
| 4,448,708 A * | 5/1984 | Killat et al. ............ 516/172 |
| 4,536,552 A * | 8/1985 | Killat et al. ............ 525/451 |
| 4,548,902 A | 10/1985 | Hasler et al. |
| 4,591,610 A | 5/1986 | Grollier |
| 4,668,508 A | 5/1987 | Grollier et al. |
| 4,848,927 A | 7/1989 | Daily et al. |
| 5,142,002 A | 8/1992 | Metzner |
| 5,866,016 A | 2/1999 | Jaquess et al. |

FOREIGN PATENT DOCUMENTS

| DE | 28 11 010 | 9/1978 |
| DE | 28 24 743 | 12/1978 |
| DE | 28 40 785 | 4/1979 |
| DE | 29 36 934 | 3/1980 |
| DE | 30 07 195 | 9/1980 |
| DE | 32 03 548 | 9/1982 |
| DE | 32 17 835 | 12/1982 |
| DE | 34 04 627 | 8/1984 |
| DE | 34 10 842 | 9/1984 |
| DE | 34 23 703 | 1/1986 |
| DE | 38 40 103 | 5/1990 |
| DE | 196 46 726 | 5/1996 |
| DE | 198 49 190 | 4/2000 |
| GB | 2 160 538 | 12/1985 |
| WO | 97/49865 | 12/1997 |

OTHER PUBLICATIONS

Revised Abstract of DE 198 49 190 A1 (English Abstract).

* cited by examiner

*Primary Examiner*—P. Hampton Hightower
(74) *Attorney, Agent, or Firm*—Oblon, Spivak, McClelland, Maier & Neustadt, P.C.

(57) ABSTRACT

The present invention relates to quaternized polyamidoamines which have at least one structural unit of the formula VII

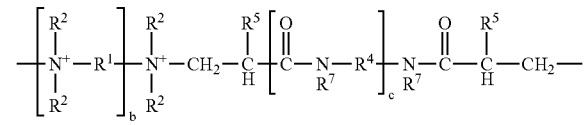

in which
$R^1$, $R^2$, $R^4$ are straight-chain or branched organic radicals optionally containing heteroatoms;
$R^5$ is hydrogen or alkyl,
$R^7$ is hydrogen or alkyl or two radicals $R^7$ together form a radical having a meaning given for $R^4$,
b is an integer from 0 to 50, and
c is an integer from 1 to 50.

Figure 1:
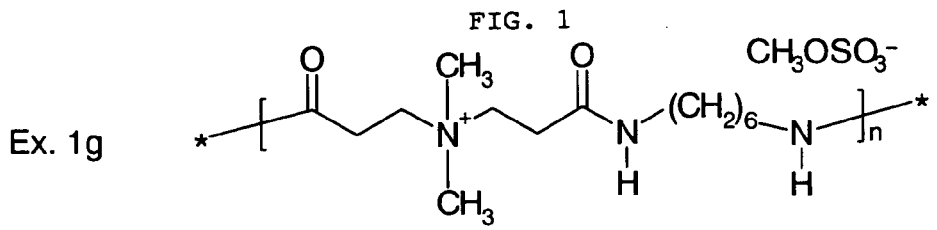
Figure 1:
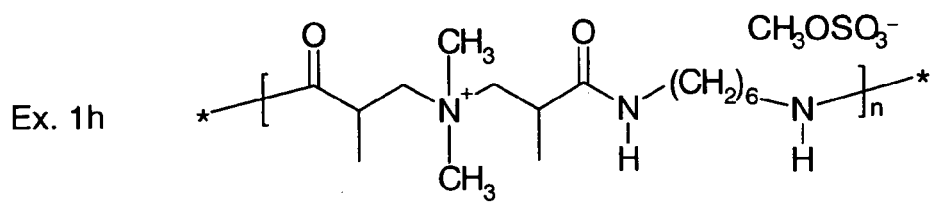
Figure 1:
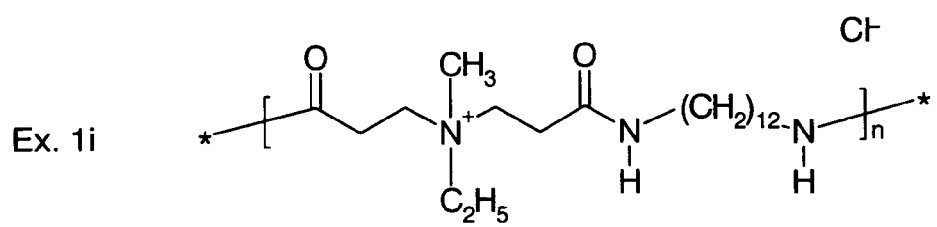
Figure 1:
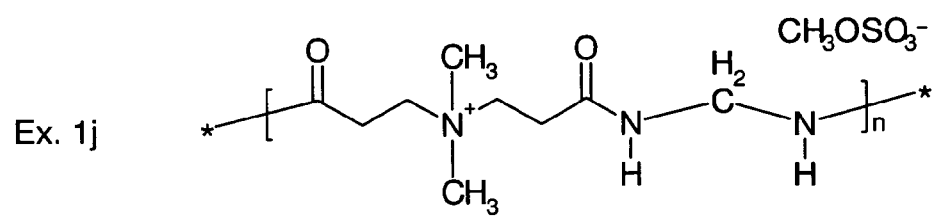
Figure 1:
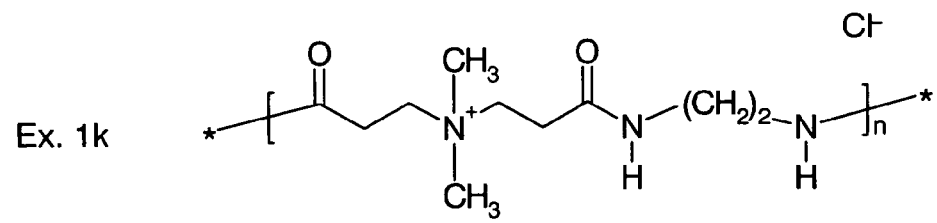
Figure 1:
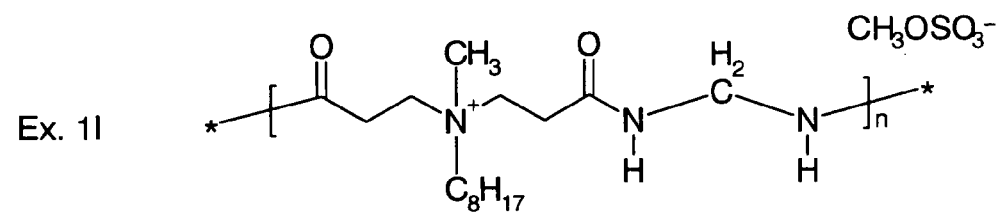
Figure 1:
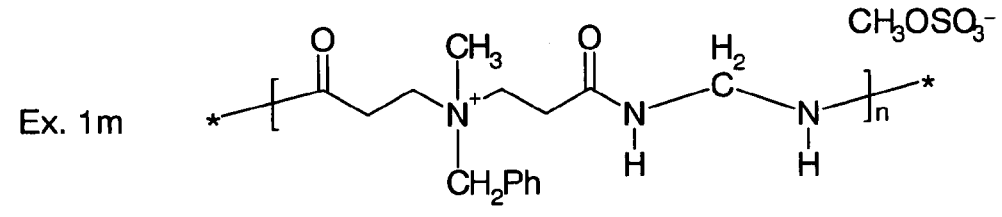
Figure 1:
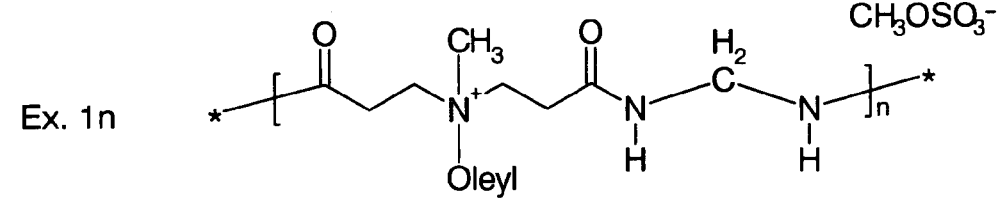

The invention also relates to the preparation of the quaternary polyamidoamines, to compositions which comprise these compounds, and to the use thereof for cosmetic and pharmaceutical purposes, and in the fields of crop protection and textile dyeing. The present invention also relates to the use of quaternized polyamidoamines of the ionene type as biostatic or biocide and thus also biocidal compositions based on quaternized polyamidoamines.

26 Claims, 3 Drawing Sheets

Ex. 1g

Ex. 1h

Ex. 1i

Ex. 1j

Ex. 1k

Ex. 1l

Ex. 1m

Ex. 1n

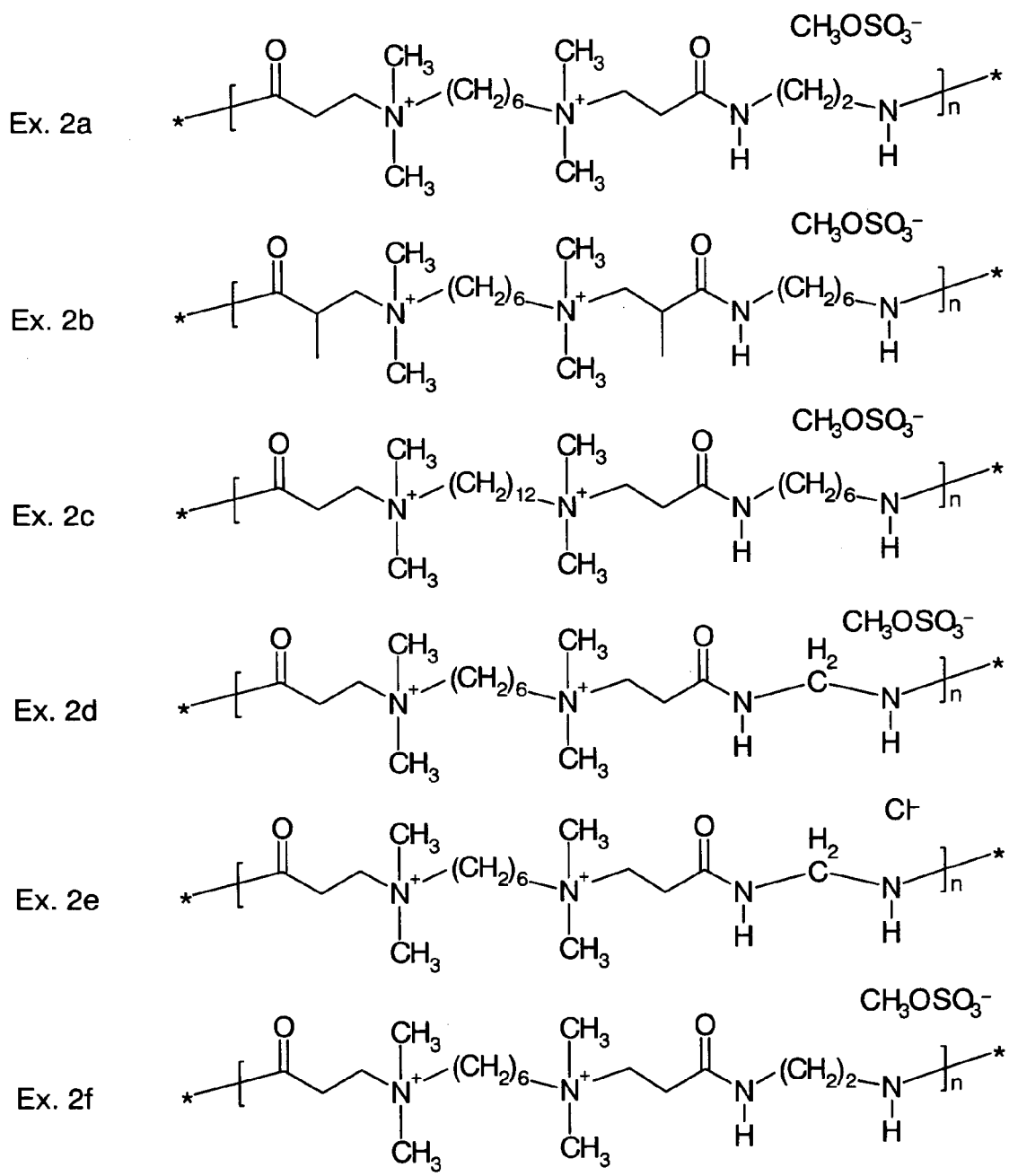

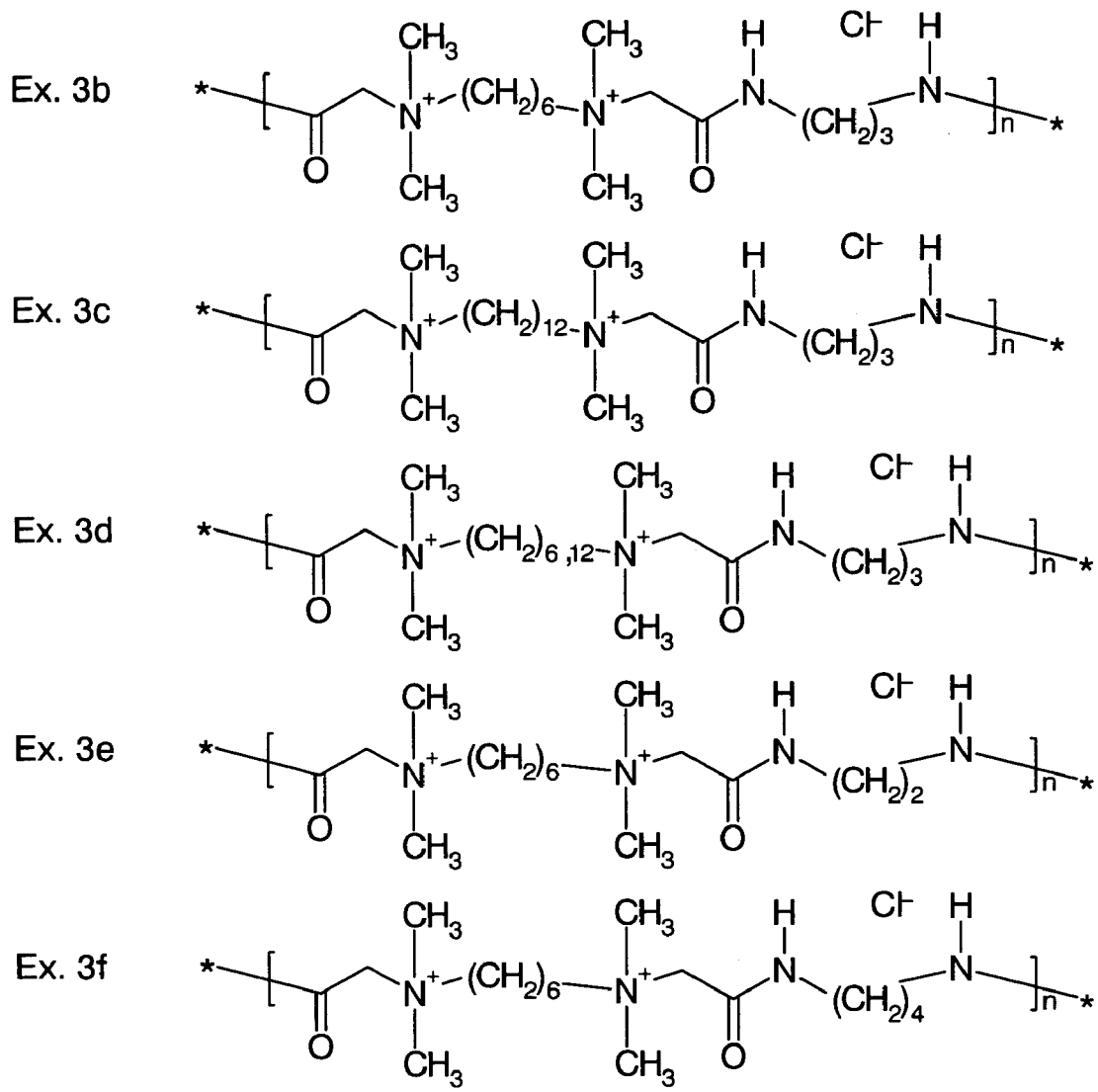

QUATERNARY POLYAMIDOAMINES, THE PRODUCTION THEREOF, CORRESPONDING AGENTS AND THE USE THEREOF

The present invention relates to certain quaternized polyamidoamines, to processes for the preparation thereof, to compositions which comprise these quaternized polyamidoamines, and to the use thereof, and also, in particular, to the use of quaternized polyamidoamines as biostatic or biocide.

Cosmetic applications of cationic polymers, eg. in shampoos, are sufficiently known. These substances, generally also referred to as quaternary polyammonium compounds also include quaternized polyamidoamines, e.g. the polymer of the formula

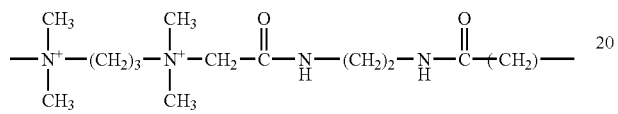

referred to in DE 29 36 934 as PAQ-1. This and similar polymers are described, for example, in DE 28 11 010, DE 28 40 785, DE 30 07 195, DE 34 04 627 and DE 34 10 842. In addition, such polymers are also mentioned in connection with the dyeing and printing of textile materials (e.g. DE 28 24 743, DE 32 03 548 and DE 32 17 835).

A particular type of polymeric quaternary ammonium compounds are the ionenes. These are polymers whose quaternized nitrogens are part of the main chain of the polymer. Various structures of such ionenes are described, for example, in U.S. Pat. No. 5,866,016.

As is known, certain quaternary ammonium compounds are valued for their biocidal effect. Benzalkonium chloride, benzethonium chloride and cetylpyridinium chloride, for example represent important disinfectants. Compared with these low molecular weight compounds, biocidal polymers often have advantages with respect to ecotoxicology, resistance development, sensitization and handleability. Poly(hexamethylenedimethylammonium) chloride, a frequently used biocide of this type, and further of these polymeric quaternary ammonium compounds are described, for example, in DE 3423703 A1 and DE 3840103 A1 and are recommended primarily for controlling microorganisms. Moreover, their use for cosmetic and medicinal purposes appears possible (cf. DE 19646726 A1).

A common disadvantage of these and numerous other biocidal polymers described in the literature is inadequate effectiveness toward certain microorganisms, for example against the widespread mold *Aspergillus niger* or toward the bacterium *Staphylococcus aureus*. In addition, many of these polymers cannot be produced cost-effectively.

Nevertheless, the spectrum of activity of biocides is an important criterion for their assessment. Ideally, a biocide should be effective against as broad a range of organisms as possible. The active concentration is also of importance. A biocide should advantageously be able to be used in the lowest possible concentration coupled with satisfactory effectiveness, meaning that no adverse effects arise for animals and humans. A rapid-onset and long-lasting effect is also often desired.

Further quaternized polyamidoamines with useful properties have now been found and, moreover, it has been established that quaternized polyamidoamines are notable for comparatively advantageous biostatic and biocidal effectiveness.

The present invention therefore provides for the use of at least one quaternized polyamidoamine as biostatic or biocide, where the polyamidoamine has at least one structural unit which is chosen from i) structural units of the formula I

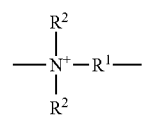

ii) structural units of the formula II

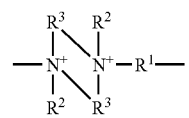

iii) structural units of the formula III

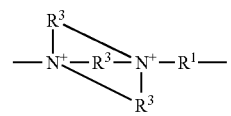

in which $R^1$, $R^2$, $R^3$ independently of one another, are straight-chain or branched, including cyclic, aliphatic or aromatic organic radicals which may include heteroatoms, and at least one of the radicals $R^1$, $R^2$ and $R^3$ has at least one amide bond.

According to the invention, the terms "biocide" and "biostatic" are used for substances which kill organisms, or inhibit growth and/or multiplication of organisms, without killing them, respectively. This effect can be directed against macroorganisms and microorganisms which may belong to the animal kingdom or the plant kingdom. From the macroorganisms, special mention is made of serpulids, crustaceans, polyps, bryozoa, hydrozoa and molluscs, for example mussels, clams and scallops. From the microorganisms special mention is made of viruses, bacteria, yeasts, fungi, diatomea and protozoa.

The use as microbiostatic or microbiocide, in particular as bacteriostatic or bacteriocide (against bacteria), fungistatic or fungicide (against yeasts and fungi), is preferred according to the invention.

A particular aspect of the present invention is the use as fungistatic or fungicide against one or more of the following yeasts:

Yeasts of the genus *Candida*, in particular *Candida albicans*; yeasts of the genus *Saccharomyces*, in particular *Saccharomyces cerevisiae*; yeasts of the genus *Geotrichum*, in particular *Geotrichum candidum*; yeasts of the genus *Pichia*, in particular *Pichia bispora*.

A further particular aspect of the present invention is the use as fungistatic or fungicide against one or more of the following fungi:

Fungi of the genus *Alternaria*, in particular *Alternaria alternata*; fungi of the genus *Aspergillus*, in particular *Aspergillus niger*; fungi of the genus *Penicillium*, in particular *Penicillium funiculum*.

A further particular aspect of the present invention is the use as bacteriostatic or bacteriocide against one or more of the following bacteria:

Gram-positive bacteria, primarily bacteria of the genus *Staphylococcus*, in particular *Staphylococcus aureus*.

The main chain of the quaternized polyamidoamines according to the invention contains at least one structural unit of the formula I, II or III. These are thus polymers of the ionene type. The main chains of the quaternized polyamidoamines generally have two or more of these structural units in repeat sequence, it being possible for these structural units to be bonded directly to one another or via linkers, and structural units bonded to one another may be identical or different. For example, the main chain may have a repeat sequence of identical structural units of the formula I, II or III. A further option is a repeat sequence of different structural units of the formula I, II or III, e.g. an alternating sequence of different structural units of the formula I, II or III which differ in one or more of the radicals $R^1$, $R^2$ and/or $R^3$. Structural units of different formulae can also be combined together, e.g. structural units of the formula I with structural units of the formulae II and/or III.

The structural units of the formulae I, II and III have radicals R which can be divided into various types. These are the radicals of the type Rx where x=1, 2, 3, thus $R^1$, $R^2$, $R^3$. In principle, it is the case for the present description that two or more radicals of the same type shown in one structural unit, structure or molecule may, despite the same name, be identical or different, and may, independently of one another, stand for one of the meanings given in each case.

A different representation numbers the radicals of a type $R^x$ in consecutive numbering with $R^{xy}$, where y=1, 2, 3, . . . . Here too, it is in principle the case that two or more radicals of type $R^x$ with different y may be identical or different.

Accordingly, the above structural units can be represented as follows:

i) structural units of the formula I':  I'

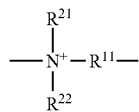

ii) structural units of the formula II':  II'

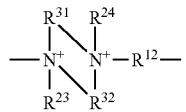

iii) structural units of the formula III':  III'

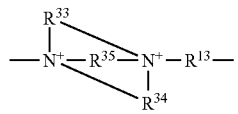

where $R^{1y}$ where y=1, 2, 3; $R^{2y}$ where y=1, 2, 3, 4; and $R^{3y}$ where y=1, 2, 3, 4, 5 may, in each case independently of one another, have the meanings given for $R^1$; $R^2$; and $R^3$, respectively.

The quaternized polyamidoamines to be used according to the invention are notable for the fact that at least one of the radicals shown in the formulae I, II and III or I', II' and III' has at least one amide bond. In one particular type of polymer, at least one of the radicals of the type $R^1$ has at least one amide bond. Of these, those polymers whose amide bonds are part of the main chain are used in particular.

A particular embodiment of quaternized polyamidoamines to be used according to the invention has, accordingly, at least one structural unit of the formula IV

IV

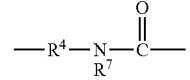

in which $R^4$ and $R^7$ may, in principle, have the meanings given in connection with $R^1$, $R^2$ and $R^3$.

In the meaning of $R^4$, the organic radicals preferably have fewer than 32 atoms, and in particular fewer than 18 atoms, in their main chain.

$R^4$ is preferably straight-chain or branched alkylene, alkenylene or alkynylene which may be substituted by one or more groups chosen, independently of one another, from halogen, cyano, hydroxyl, alkoxy, thioalkyl, acyl, acyloxy, alkoxycarbonyl, carboxy, amino, and may be interrupted by one or more groups chosen, independently of one another, from O, S, CO, NH, N(alkyl), arylene and cycloalkylene.

Particularly preferably, $R^4$ is a group of the formula V

V

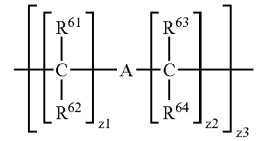

in which $R^{61}$, $R^{62}$, $R^{63}$, $R^{64}$, independently of one another, are hydrogen, hydroxyl or alkyl optionally substituted by OH;

A is a bond, O, S, CO, OC(O), (O)CO, NHCO, CONH, arylene, in particular phen-1,4-ylene, biphen-4',4'-ylene, cycloalkylene, in particular cyclohex-1,4-ylene, z1, z2, independently of one another, are an integer from 0 to 32, preferably from 0 to 18, and the sum of z1 and z2 corresponds to an integer from 1 to 32, preferably 1 to 18, and z3 is an integer from 1 to 10, preferably from 1 to 3.

If z3 is greater than 1, then two or more indices z1 (z1', z1", . . . ) or z2 (z2', z2", . . . ) arise, as do two or more radicals A and $R^{61}$, $R^{62}$, $R^{63}$, $R^{64}$, which in each case may be identical or different, but are preferably identical, meaning that, in this case, $R^4$ forms from a sequence of identical structural units of the formula V, e.g. ethylene oxide units or propylene oxide units, and, for example, has a polyethylene oxide structure, polypropylene oxide structure, polyamide structure or polyurethane structure. Particularly preferred quaternized polyamidoamines arise if A is a bond, 0, phen-1,4-ylene or biphen-4',4'-ylene, $R^{61}$, $R^{62}$, $R^{63}$, $R^{64}$ are all hydrogen, and the sum of z1 and z2 corresponds to a value from 1 to 32, preferably 1 to 18. In addition, there is a preference for radicals $R^4$ which satisfy one, more than one or all of the following criteria: linearity, symmetry, no heteroatom.

$R^4$ is very particularly preferably $C_{1-32}$-alkylene and in particular $C_{1-18}$-alkylene, and of these primarily the linear radicals, in particular methylene, eth-1,2-ylene, prop-1,3-ylene, hex-1,6-ylene and dodecan-1,12-ylene.

The radicals of the type $R^1$, i.e. in particular $R^{1y}$ where y=1, 2, 3, are divalent radicals. $R^1$ is a straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene.

$R^1$ is particularly preferably a group of the formula V having the meanings given above.

Very particularly preferably, the radicals $R^1$ are straight-chain or branched $C_{1-32}$-alkylene having, preferably, 1 to 18 and, in particular, 4 to 14 carbon atoms.

The radicals of type $R^2$, i.e. in particular $R^{2y}$ where y=1, 2, 3, 4, are monovalent radicals. These radicals are preferably straight-chain or branched alkyl, alkenyl or aralkyl which may be substituted by groups chosen independently of one another from alkyl, halogen, cyano, hydroxyl and alkoxy, and may be interrupted by one or more groups chosen independently of one another from O, S, CO, NH and N(alkyl), or two radicals $R^2$ form, together with the nitrogen to which they are bonded, a corresponding cyclic radical, e.g. a pyrrolidinium, morpholinium or piperidinium radical, or together form a radical bonded to different quaternized nitrogens which can have a meaning given below in connection with $R^3$. Those radicals $R^2$ which do not have an amide bond are primarily alkyl, alkenyl and aralkyl radicals having up to 32 carbon atoms, in particular short-chain alkyl radicals having up to 10 carbon atoms, but also long-chain, primarily fatty acid-derived radicals having more than 10 carbon atoms which may be saturated or unsaturated, such as oleyl, or phenylalkyl radicals having preferably 1 to 3 carbon atoms in the alkyl moiety. Accordingly, particularly preferred radicals of type $R^2$ are optionally hydroxyl-substituted $C_{1-8}$-alkyl radicals, and of these particular mention should be made of methyl, ethyl, isopropyl, t-butyl and octyl or hydroxymethyl and hydroxyethyl, palmityl, stearyl, lauryl and oleyl, or benzyl.

The radicals of type $R^3$, i.e. in particular $R^{3y}$ where y=1, 2, 3, 4, 5, are divalent radicals which link quaternized nitrogen atoms together. These radicals are preferably straight-chain or branched alkylene, alkenylene or alkynylene which may be substituted by one or more groups chosen independently from halogen, cyano, hydroxyl and alkoxy, and may be interrupted by one or more groups chosen independently of one another from O, S, CO, NH and N(alkyl). In the meaning of $R^3$, alkylene, alkenylene and alkynylene preferably have up to 3 carbon atoms. Radicals of the type $R^3$ primarily stand for $C_{1-3}$-alkylene, in particular eth-1,2-ylene and prop-1,3-ylene. Accordingly, preferred structural units of the formulae II are quaternized piperazines.

According to a particular embodiment, the present invention relates to quaternized polyamidoamines which have at least one structural unit of the formula VII

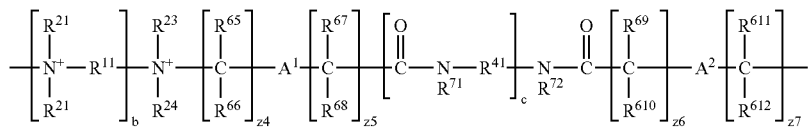

in which $R^{11}$, $R^{21}$, $R^{22}$, $R^{23}$, $R^{24}$, $R^{41}$, $R^{65}$, $R^{66}$, $R^{67}$, $R^{68}$, $R^{69}$, $R^{610}$, $R^{611}$, $R^{612}$, $A^1$, $A^2$, z4, z5, z6, z7, $R^{71}$, $R^{72}$ may have meanings given in connection with the radicals of type $R^1$, $R^2$, $R^4$, $R^6$, A, z1, z2, and $R^7$, b is an integer from 0 to 50, and c is an integer from 1 to 50.

According to a preferred variant, $A^1$, $A^2$ are in each case a bond, $R^{65}$, $R^{66}$, $R^{67}$, $R^{68}$, $R^{69}$, $R^{610}$, $R^{611}$, $R^{612}$ are all hydrogen or methyl, and the sum of z4 and z5 or z6 and z7 corresponds to a value from 1 to 32, thus giving rise to linear or branched $C_{1-32}$-alkylene having preferably 1 to 8 and especially 1 to 3 carbon atoms, in particular methylene, eth-1,2-ylene or prop-1,2-ylene.

Structural units of the formula VII may also realize structural units of the formulae II or III by two of the radicals which are per se monovalent together forming a divalent radical of the type $R^3$, which links two quaternized nitrogens, and also $R^{11}$ assuming the meaning of a radical $R^3$.

This structural unit of the formula VII is composed of b+1 structural units of the formula I. Accordingly, the structural unit of the formula VII may illustrate a sequence of different structural units of the formula I with different radicals $R^1$, where $R^{11}$ corresponds in particular to a radical $R^1$ which does not have an amide bond.

If b and/or c are greater than 1, then the radicals of identical designation which arise may have identical or different meanings.

According to another aspect, structural units of the formula VII in which b=0 or 1 and c=1 are preferred.

If b=1, then $A^1$, $A^2$ are in particular in each case a bond, if $R^{65}$, $R^{66}$, $R^{67}$, $R^{68}$, $R^{69}$, $R^{610}$, $R^{611}$, $R^{612}$ are preferably all hydrogen, and if the sum of z4 and z5 or z6 and z7 corresponds to a value from 1 to 32, then linear or branched $C_{1-32}$-alkylene having preferably 1 to 8 and especially 1 to 3 carbon atoms, in particular methylene, arises (type A); or if $A^1$, $A^2$ are in particular in each case a bond, if $R^{65}$, $R^{66}$, $R^{67}$, $R^{68}$, $R^{69}$, $R^{610}$, $R^{611}$, $R^{612}$ are preferably hydrogen or methyl, and if the sum of z4 and z5 or z6 and z7 corresponds to a value of 2, then linear or branched $C_{2-32}$-alk-1,2-ylene having preferably 2 to 8 and especially 2 or 3 carbon atoms, in particular eth-1,2-ylene or prop-1,2-ylene, arises (type C). If b=0, then A is in particular a bond, if $R^{65}$, $R^{66}$, $R^{67}$, $R^{68}$, $R^{69}$, $R^{610}$, $R^{611}$, $R^{612}$ are preferably hydrogen or methyl, and if the sum of z4 and z5 or z6 and z7 corresponds to a value of 2, then linear or branched $C_{2-32}$-alk-1,2-ylene having preferably 2 to 8 and especially 2 or 3 carbon atoms, in particular eth-1,2-ylene or prop-1,2-ylene, arises (type B).

Quaternary polyamidoamines preferably used according to the invention have at least one structural unit of the formula VIIA

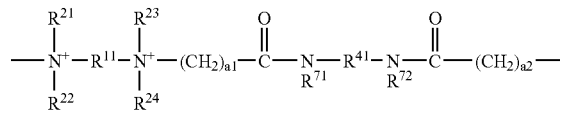

in which the radicals $R^{11}, R^{21}, R^{22}, R^{23}, R^{24}, R^{41}, R^{71}, R^{72}$ have the meanings given above, and a1, a2, independently of one another, are an integer from 1 to 32.

The present invention further provides in particular the above-described quaternized polyamidoamines which have at least one structural unit of the formula VIIBC

VIIBC

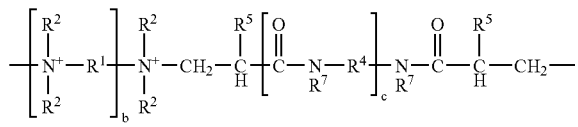

in which $R^1, R^2, R^4$ are straight-chain or branched, cyclic closed organic, i.e. aliphatic or aromatic, radicals which may include heteroatoms;

$R^5$ is hydrogen or alkyl, $R^7$ is hydrogen or alkyl or two radicals $R^7$ together form a radical with a meaning given for $R^4$, b is an integer from 0 to 50, and c is an integer from 1 to 50.

A different representation numbers the radicals of a type $R^x$ in consecutive numbering with $R^{xy}$, where y=1, 2, 3, . . . . Here too, it is in principle the case that two or more radicals of a type $R^x$ with different y may be identical or different.

Accordingly, the above structural units can be represented as follows:

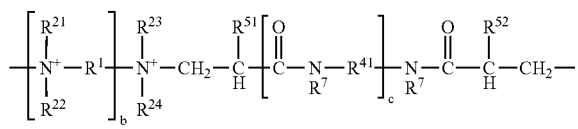

where $R^{1y}$ where y=1; $R^{2y}$ where y=1, 2, 3, 4; $R^{4y}$ where y=1; $R^{5y}$ where y=1, 2; $R^{7y}$ where y=1, 2 may, in each case independently of one another, have the meanings given for $R^1$; $R^2$; $R^4$; $R^5$; and $R^7$, respectively.

According to the invention, preference is given to quaternary polyamidoamines which have at least one structural unit of the formula VIIB and/or VIIC

VIIB

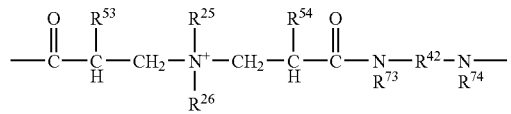

VIIC

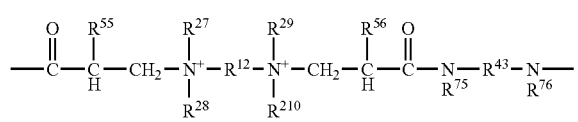

in which the radicals $R^{12}, R^{25}, R^{26}, R^{27}, R^{28}, R^{29}, R^{210}, R^{42}, R^{43}, R^{73}, R^{74}, R^{75}, R^{76}$ have the meanings given above, and $R^{53}, R^{54}, R^{55}, R^{56}$, independently of one another, are hydrogen or alkyl, preferably methyl.

Preferably, in the formulae VIIA or VIIB or VIIC $R^{11}, R^{12}$ are straight-chain or branched $C_{1-32}$-alkylene, $R^{21}, R^{22}, R^{23}, R^{24}, R^{25}, R^{26}, R^{27}, R^{28}, R^{29}, R^{210}$, independently of one another, are optionally substituted $C_{1-32}$-alkyl, $C_{2-32}$-alkenyl or benzyl, $R^{41}, R^{42}, R^{43}$, independently of one another, are $C_{1-18}$-alkylene, $R^{71}, R^{72}, R^{73}, R^{74}, R^{75}, R^{76}$, independently of one another, are hydrogen or in each case two of the radicals are eth-1,2-ylene.

In structural units of the formula VIIA or VIIC, $R^{11}$ and $R^{12}$ are preferably $C_{1-32}$-alkylene and in particular $C_{1-18}$-alkylene. $R^{11}$ and $R^{12}$ are more preferably $C_{4-14}$-alkylene, and of these in particular the linear radicals, particular mention being made of hex-1,6-ylene and dodecan-1,12-ylene. $R^{21}, R^{22}, R^{23}, R^{24}, R^{25}, R^{26}, R^{27}, R^{28}, R^{29}, R^{210}$ in the formulae VIIA, VIIB or VIIC are primarily methyl, ethyl and octyl as preferred $C_{1-32}$-alkyl radicals, are oleyl as preferred $C_{2-32}$-alkenyl radical, or are benzyl as preferred aralkyl radical, where 2 radicals positioned on the same quaternized nitrogen may be different, but are preferably identical. According to a particular variant of the formula VIIA or VIIC, $R^{21}$ and $R^{23}$ or $R^{27}$ and $R^{29}$ together form divalent radicals $R^3$, preferably eth-1,2-ylene, and $R^{11}$ and $R^{12}$ are also a divalent radical of the type $R^3$, preferably eth-1,2-ylene. Dialkylpiperazinium derivatives arise as preferred structural element of this variant.

$R^{41}, R^{42}, R^{43}$ in the formula VIIA, VIIB or VIIC are preferably $C_{1-18}$-alkylene. In the meaning of $R^{41}$ and $R^{43}$ of the formula VIIA or VIIC, these alkylene radicals advantageously have 1 to 6 carbon atoms, while in the meaning of $R^{42}$ of the formula VIIB, these radicals advantageously have 6 to 18 carbon atoms. Meanings for $R^{41}$ or $R^{43}$ which are to be mentioned in particular are methylene, eth-1,2-ylene and prop-1,3-ylene; for $R^{42}$, mention may be made in particular of hex-1,6-ylene and dodecan-1,12-ylene.

$R^{53}, R^{54}, R^{55}, R^{56}$ of the formula VIIB or VIIC are preferably hydrogen or methyl.

$R^{71}, R^{72}, R^{73}, R^{74}, R^{75}, R^{76}$ are preferably hydrogen.

The values of a1, a2 of the formula VIIA are preferably 1.

The positive charge of the quaternized polyamidoamines according to the invention requires counteranions. Suitable counteranions are, in principle, any inorganic and organic mono-, di- and also polyvalent anions. These counteranions usually arise from the chosen preparation process. In this case, counteranions are primarily anions which function as leaving group in a nucleophilic substitution, for example halides and sulfates. It is, however, also possible to exchange the counteranions resulting from the preparation process with other anions.

The counteranions of quaternized polyamidoamines according to the invention are preferably chosen from halides, in particular chloride or bromide, alkylsulfates, in particular methylsulfate and ethylsulfate, phosphates, and carboxylates, in particular succinates.

The polyamidoamines which can be used according to the invention preferably have repeat sequences of the above-described structural units. These may be continuous sequences of identical, repeat structural units (repeat units), alternating sequences of different repeat units or any desired sequences of different repeat units.

A preferred polyamidoamine consists essentially of identical or different repeat units of the formula VII.

This polymer can be represented by the formula VIII:

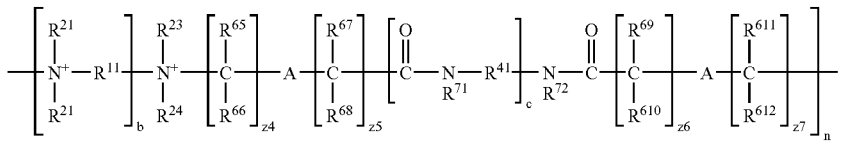

in which the given radicals can have the above meanings and n corresponds to a value from 3 to 200. It may be noted that this representation also describes sequences of different structural units of the formula VII which differ in the meaning of at least one of the radicals shown. Overall, the polymer has n structural units of the formula VII which may be identical or different.

Based on an individual polymer chain, n is an integer. However, in practise, use is usually made of mixtures of polymer chains which may have different values of n, meaning that the value of n is an average value. n is preferably in a range from 3 to 200 and in particular from 10 to 150.

A particular embodiment (type A) of these polyamidoamines consists essentially of repeat units of the formula VIIA and can be represented diagrammatically by the following formula VIIIA.

VIIIA

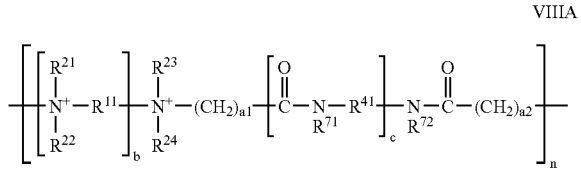

where $R^{11}$, $R^{21}$, $R^{22}$, $R^{23}$, $R^{24}$, $R^{41}$, $R^{71}$, $R^{72}$, a1, a2, b, c and n have the meanings given above and the value of b is at least 1.

A further particular embodiment (type BC) of these polyamidoamines consists essentially of repeat units of the formula VIIBC and can be represented diagrammatically by the following formula VIIIBC:

VIIIBC

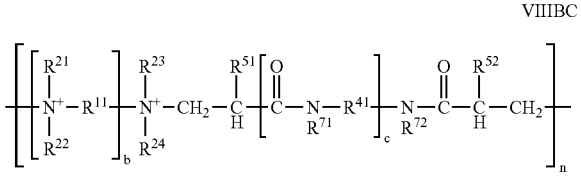

A particular embodiment (type B) of these polyamidoamines consists essentially of repeat units of the formula VIIB and can be represented diagrammatically by the following formula VIIIB:

VIIIB

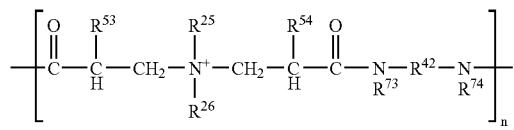

where $R^{25}$, $R^{26}$, $R^{42}$, $R^{53}$, $R^{54}$, $R^{73}$, $R^{74}$ and n have the meanings given above.

A further particular embodiment (type C) of these polyamidoamines consists essentially of repeat units of the formula VIIC and can be represented diagrammatically by the following formula VIIIC:

VIIIC

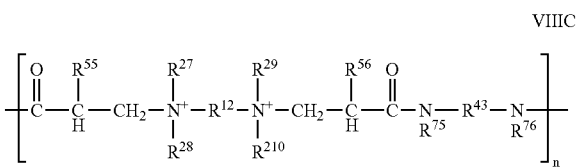

in which $R^{12}$, $R^{27}$, $R^{28}$, $R^{29}$, $R^{210}$, $R^{43}$, $R^{55}$, $R^{56}$, $R^{75}$, $R^{76}$ and n have the meanings given above.

Advantageously, n is greater than 10 and in particular greater than 20.

The polymers which can be used according to the invention preferably have a weight-average molecular weight $M_W$ of at least 500 g/mol and in particular of at least 2500 g/mol. The weight-average molecular weight is advantageously in a range from 10 000 to 50 000. The weight-average molecular weight can be determined, for example, by means of $C^{13}$ end-group analysis.

The polyamidoamines can be prepared in a manner known per se. Thus, it is possible, for example, to alkylate corresponding tertiary diamines with suitable difunctional amides or to react corresponding a,b-unsaturated carboxylic acid derivatives, for example esters or even amides, with primary amines or primary or secondary diamines in a Michael addition to give tertiary amines and, where necessary, to react the esters with primary or secondary diamines to give the amides, and to quaternize the adducts.

The present invention therefore provides a process for the preparation of quaternized polyamidoamines by reacting a compound of the formula X

X

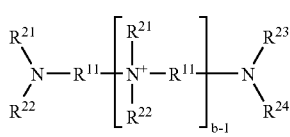

in which $R^{11}$, $R^{21}$, $R^{22}$, $R^{23}$, $R^{24}$ and b have the meanings given above, in particular in connection with formula VIIA, with a compound of the formula XI

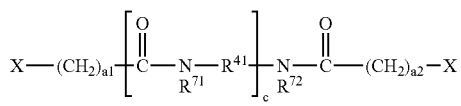

XI in which $R^{41}$, $R^{71}$, $R^{72}$, a1, a2 and c have the meanings given above, in particular in connection with formula VIIA, and X is a suitable leaving group, such as Cl, Br or I.

The reactants are usually used in a molar ratio of about 1:1. It is advantageous to firstly dissolve one of the reactants in a solvent or solvent mixture and then to add the other reactants. The compound of the formula XI is preferably dissolved first. Preference is given to polar solvents or solvent mixtures, for example alcohols, such as methanol or ethanol, dimethylformamide, acetonitrile and the like. A solvent mixture of methanol and DMF or acetonitrile has proven useful. The choice of solvent or solvent mixture is made depending on the nature and, in particular, the solubility behavior of the resulting polymer. A smooth reaction should be ensured without the polymer precipitating out too quickly. It has proven useful to dissolve the compound of the formula XI in the solvent or solvent mixture in a weight ratio of about 1:1. The compound of the formula X is usually added in portions, advantageously by adding dropwise. The feed can be controlled such that the desired reaction temperature is established. This reaction temperature during the feed is expediently about 10 to about 40° C. and advantageously about 20 to 30° C. If required, heat may also be introduced or removed, in particular the reaction temperature can be increased when the feed is complete, expediently to about 50 to 80° C. and preferably about 60 to 70° C. The reaction is complete when further conversion can no longer be measured. Following conclusion of the reaction, the mixture can be diluted with further solvent, for example water. Subsequent ultrafiltration, for example over a 5 kD membrane has proven useful. Further work-up and isolation of the polymer can take place by customary methods, for example freeze-drying, fluidized-bed drying, spray-drying and the like.

In the case of less reactive compounds of the formula XI, the rate of the reaction can be increased by adding some potassium iodide. The molecular weight of the polymer can be influenced by varying the stoichiometric ratio of the reactants in a manner known per se.

The compounds of the formula XI can also be prepared in a manner known per se. For example, a corresponding primary or secondary diamine of the formula XIIA

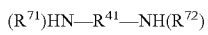 XIIA in which $R^{41}$, $R^{71}$, $R^{72}$ have the meanings given above, in particular in connection with formula VIIA, can be reacted with compounds of the formula XIII

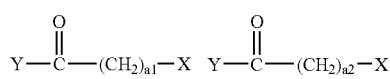

XIII in which X, a1, a2 have the meanings given above, in particular in connection with formula VIIA, and Y is a halide or another group active in the amide synthesis, in a manner known per se.

The compounds of the formula XIII are thus expediently carboxylic acid halides or other carboxylic acid derivatives which are reactive in the amide synthesis.

Quaternized polyamidoamines which result from this process have X-anions as counteranions.

The present invention also provides for the use of the quaternized polyamidoamines obtainable by this process. These are primarily quaternized polyamidoamines which have structural units of the formula VIIA, i.e. in particular polyamidoamines of the formula VIIIA, and preferred embodiments thereof.

The present invention also provides a process for the preparation of quaternized polyamidoamines by a) Michael addition of a primary amine of the formula XIV

 XIV in which $R^{25}$, $R^{26}$ have the above meanings given in particular in connection with formula VIIIB, with at least two equivalents of an a,b-unsaturated carboxylic acid or of a derivative thereof of the formula XV

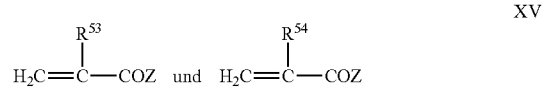

XV in which $R^{53}$, $R^{54}$ have the above meanings given in particular in connection with formula VIIIB, and Z is hydroxyl or alkoxy;

b) optional quaternization of the adduct of the formula XVI resulting in stage a)

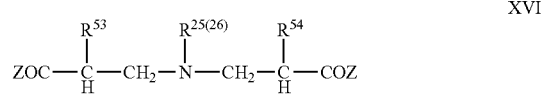

XVI in which $R^{25}$, $R^{26}$, $R^{53}$, $R^{54}$, Z have the above meanings given in particular in connection with formula VIIIB, c) reaction of the adduct of the formula XV resulting in stage a) or of the quaternization product of the formula XVII resulting in stage b)

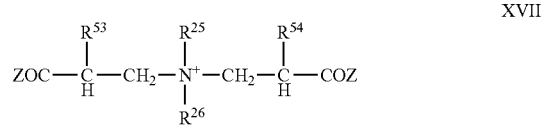

XVII in which $R^{25}$, $R^{26}$, $R^{53}$, $R^{54}$, Z have the above meanings given in particular in connection with formula VIIIB, with a diamine of the formula XVIII

 XVIII in which $R^{42}$, $R^{73}$, $R^{74}$ have the above meanings given in particular in connection with formula VIIIB, d) optional quaternization of the polyamidoamine of the formula XIX resulting in stage c)

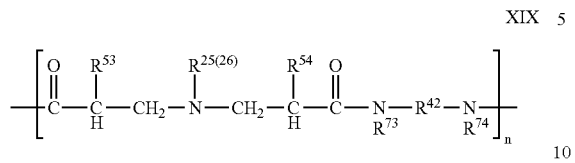
XIX in which $R^{25}$, $R^{26}$, $R^{42}$, $R^{53}$, $R^{54}$, $R^{73}$, $R^{74}$ have the above meanings given in particular in connection with formula VIIIB.

In stage a) the reactants are usually reacted in a molar ratio of 1:2 of primary amine of the formula XIV to α,β-unsaturated carboxylic acid (derivative) of the formula XV, in particular a carboxylic acid ester. For this, the reactants are mixed together, for example the compound with the formula XIV can be introduced into the compound of the formula XV. To carry out stage b), it is expedient to add solvent to the adduct of the formula XVI resulting in stage a). For example, the adduct can be mixed in equal parts with the alcohol which corresponds to the ester-forming alcohol of the carboxylic acid. If ethyl acrylate or ethyl methacrylate is used, then ethanol is suitable. The quaternizing agent is usually added in a molar ratio of 1:1, based on the primary amine used in stage a). Suitable quaternizing agents are known per se and are chosen depending on the desired radical $R^{25}$ or $R^{26}$ and the desired counteranion. Suitable quaternizing agents include, for example, alkyl halides, in particular methyl chloride, dialkyl sulfates, in particular dimethyl sulfate and diethyl sulfate, and ethylene oxide. The quaternized amine resulting in stage b) can expediently be taken up in a further solvent and is then reacted with a suitable diamine of the formula XVIII in stage c). For this, diamine is generally used in a molar ratio of about 1:1 based on the amine used in stage a). The esterification reaction can be carried out in a manner known per se. For the variant in which the adduct of the formula XVI resulting in stage a) is not quaternized, but is reacted with the diamine of the formula XVIII and then the polyamidoamine of the formula XIX resulting in stage c) is quaternized, the above statements apply correspondingly. The further measures for working up and isolating the polymer can be carried out analogously to the procedure described above. Products which are insoluble in water can be reprecipitated from suitable aqueous solvent mixtures, for example acetone/water.

The present invention also provides the quaternized polyamidoamines obtainable by this process which have structural units of the formula VIIB, i.e. in particular polyamidoamines of the formula VIIIB, and preferred embodiments thereof.

An alternative to the above-described diester synthesis which is to be described and is further provided by the invention is a diacrylate synthesis process according to which the diamine of the formula XVIII is firstly reacted with approximately two equivalents of the α,β-unsaturated carboxylic acid or a derivative thereof of the formula XV to give the diacrylate of the formula XX. By a) Michael addition of a compound of the formula XIV $H_2N-R^{25(26)}$     XIV in which $R^{25}$, $R^{26}$ have the above meanings given in particular in connection with formula VIIIB, with at least one equivalent of an α,β-unsaturated carboxylic acid diamine of the formula XX

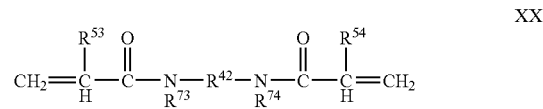
XX in which $R^{42}$, $R^{53}$, $R^{54}$, $R^{73}$, $R^{75}$ have the above meanings given in particular in connection with formula VIIIB, and b) quaternization of the polyamidoamine of the formula XIX resulting in stage a)

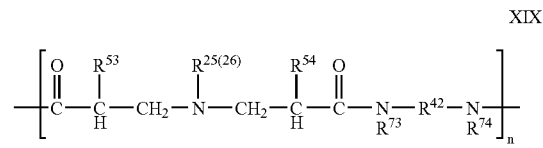
XIX where $R^{25}$, $R^{26}$, $R^{42}$, $R^{53}$, $R^{54}$, $R^{73}$, $R^{74}$ have the above meanings given in particular in connection with formula VIIIB, quaternized polyamidoamines which have structural units of the formula VIIB, i.e. in particular polyamidoamines of the formula VIIIB, and preferred embodiments thereof, are obtainable.

Thus, it is possible to slurry the bisarylamide of the formula XX in a suitable solvent or solvent mixture, e.g. aqueous alcohol, and to add the amine of the formula XIV. The reaction temperature is expediently at about 10 to about 40° C. and advantageously about 20 to 30° C. Reaction times of from a few hours to days are usually required. For example, the reaction mixture can firstly be stirred at room temperature for 24 hours and then at about 30° C. for a further 48 hours. The resulting polymer can then be isolated and slurried again, e.g. in methanol. Quaternizing agent is then added dropwise, expediently in a slight excess, until a clear solution is present. Where necessary, the mixture is further stirred, and the temperature is increased to about 30 to 80° C., preferably about 50 to 70° C. Following removal of the solvent, the residue can be taken up in water and dialyzed.

The present invention further provides a process for the preparation of quaternized polyamidoamines, the procedure being carried out in an analogous manner via the process stages given in connection with the diester or diacrylate synthesis and, in stage a), instead of the primary amine of the formula XIV, a primary or secondary diamine of the formula XXI

XXI being used, in which $R^{12}$, $R^{27}$, $R^{28}$, $R^{29}$, $R^{210}$ have the above meanings given in particular in connection with formula VIIIC.

Thus, the present invention further also provides the quaternized polyamidoamines obtainable by this process which have structural units of the formula VIIC, i.e. in particular polyamidoamines of the formula VIIIC, and preferred embodiments thereof.

In addition to the end-groups which arise depending on the process, the quaternary polyamidoamines according to the invention can also have specific end-groups. These can be introduced in a manner known per se, for example by using one reactant in excess. It is also possible to react certain amounts of monofunctional tertiary amines or monofunctional substituted or unsubstituted alkyl halides with the polymer.

Furthermore, the quaternized polyamidoamines can also be crosslinked, appropriate measures are known per se to the person skilled in the art.

The representations according to the formulae of polymers according to the invention given in the scope of the present description have essentially linear polymer sections, although it is entirely possible for the polymers to also have branches. These result in many cases from secondary reactions in which, for example, a nitrogen reacts a number of times in the manner described above.

Being cationic polymers, the quaternized polyamidoamines according to the invention have many useful applications. Examples which may be mentioned here are, in the cosmetics sector, the treatment of keratin, in particular of hair for conditioning or setting; in the fields of pharmacy, crop protection and textile dyeing, e.g. in cellulose dyeing or the aftertreatment of dyeings.

Corresponding compositions which, as well as comprising at least one polyamidoamine according to the invention, comprise active ingredients and/or auxiliaries are just as well known to the person skilled in the art as their preparation.

The use according to the invention as biostatic or biocide includes a method for inhibiting growth and/or replication, or killing of organisms. In this connection, use is made of at least one quaternized polyamidoamine of the type described above in an amount with which the desired effect can be achieved. This amount depends on the type of desired treatment and can be ascertained in an expert manner.

The treatment can be carried out for medicinal, in particular dermatological, and cosmetic purposes, for preservation and cleaning purposes. The aim is to control the amount of particular organisms locally or spatially. Control means prevention, reduction to a desired level and/or elimination. For example, methods of disinfection (degermination), removal of algae, for control of the adhesion of organisms to surfaces (antifouling), for the control of odors, discolorations and the like belong to this circle of application.

In particular, it is possible to treat fluids, in particular water and aqueous systems, and also surfaces which are at least partially in contact therewith. For example, water which is used industrially and for sanitation, or surfaces which can come into contact with this water can be treated. Such surfaces are found, for example, in cooling towers, pumps, heat exchangers, various pipelines and in bathing installations. The process according to the invention can also advantageously be used for papermaking and the manufacture of textiles.

The quaternized polyamidoamines according to the invention are expediently applied in accordance with the nature of the object to be treated. Thus, the application may take place, for example, by dissolution, suspension, or emulsification in a fluid to be treated or by application to a surface, for example by immersion, spraying or painting.

The quaternized polyamidoamines are generally formulated in accordance with medicinal, cosmetic or other relevant practice. For example, the treatment usually takes place by single or multiple application of compositions which comprise at least one of the quaternized polyamidoamines described above. As well as quaternized polyamidoamines, such compositions can comprise further active ingredients, in particular other biostatics or biocides, and/or customary auxiliaries.

According to a particular embodiment of the present invention, the composition comprises, as further active ingredient, at least one ionene with structural units of the formula IX

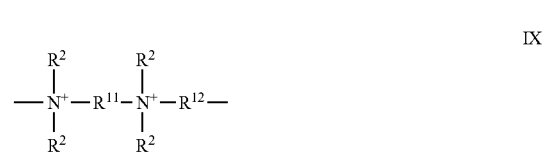

where the radicals $R^{11}$, $R^{12}$, $R^2$ may in principle represent any desired organic radicals in accordance with the statements relating to polyamidoamines according to the invention.

Preferably, $R^{11}$ is $C_{1-8}$-alkylene, $R^{12}$ is $C_{8-24}$-alkylene and $R^2$ is $C_{1-3}$-alkyl.

An ionene preferred as further active ingredient consists essentially of identical or different repeat units of the formula IX and can be represented by the following formula IXA:

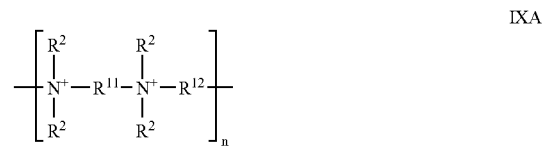

where $R^{11}$, $R^{12}$ and $R^2$ have the meanings given above and n is an integer from 10 to 300.

Further configurations of this ionene type arise in an analogous manner from the above statements relating to the radicals of the type $R^1$, $R^2$ and $R^3$. Ionenes of the formula IX, in which $R^1$ is hex-1,6-ylene, $R^2$ is dodecan-1,12-ylene, $R^3$ is methyl and n is a number from 10 to 150 can advantageously be combined with the polyamidoamines according to the invention. In particular, the spectrum of activity of biocidal or biostatic compositions according to the invention can be extended. In particular, the effect against *Staphylococcus aureus*.

Further active ingredients to optionally be used in combination with polyamidoamines according to the invention are oxidizing agents, for example peroxides, such as sodium persulfate, potassium persulfate or hydrogen peroxide; and certain metal salts, in particular copper and silver salts.

Suitable formulation bases and advantageous auxiliaries are sufficiently known to the person skilled in the art.

Compositions according to the invention generally comprise

5–100% by weight of an active ingredient component and

0–95% by weight of an auxiliary component. The sum of active ingredient component and auxiliary component is 100% by weight.

The active ingredient component comprises at least one quaternized polyamidoamine and can comprise further active ingredients. The proportion of quaternized polyamidoamines, based on the active ingredient component, is preferably at least 10% by weight and in particular at least 25% by weight. According to a particular embodiment, the active ingredient component consists of one or more polyamidoamines according to the invention.

The compositions may be solid forms, for example powders, granules or tablets, semisolid forms, for example ointments, creams, gels and pastes, liquid forms, for example solutions, emulsions and suspensions. Aerosols may also be suitable. Further application forms which can be used and the choice of an appropriate form are part of the expert configuration of the present invention.

Depending on the intended use, they may be pharmaceutical, in particular dermatological, cosmetic, preserving, cleaning, in particular disinfecting, and surface infestation-preventing (antifouling) compositions.

Terms such as alkyl, alkoxy, thioalkyl etc. include straight-chain or branched hydrocarbon groups, such as $CH_3$, $C_2H_5$, n-propyl, $CH(CH_3)_2$, n-butyl, $CH(CH_3)C_2H_5$, 2-methylpropyl, $C(CH_3)_3$, n-pentyl, n-hexyl, n-heptyl or n-octyl, in particular $CH_3$, $C_2H_5$, $CH(CH_3)_2$ or $C(CH_3)_3$, preferably with—unless stated otherwise—1 to 32, primarily 1 to 22, in particular 1 to 10 and particularly preferably 1 to 4, carbon atoms.

The term "alkenyl" includes straight-chain or branched, mono- or poly-, preferably di- or tri-, unsaturated hydrocarbon groups, preferably having—unless stated otherwise—2 to 32, primarily 2 to 22, carbon atoms. The same applies for "alkynyl".

The term "cycloalkyl" includes mono- or bicyclic saturated hydrocarbon groups, such as cyclopropyl, cyclobutyl, cyclopentyl, cyclohexyl, etc., preferably having—unless stated otherwise—3 to 9, in particular 3 to 6 and particularly preferably 5 or 6, carbon atoms.

"Aryl" is preferably naphthyl and in particular phenyl.

"Aralkyl" is preferably aryl, in particular naphthyl and primarily phenyl which is bonded to an alkylene radical. Particular preference is given to benzyl.

The term "alkylene" includes straight-chain or branched radicals, such as methylene, eth-1,1-ylene, eth-1,2-ylene, prop-1,1-ylene, prop-1,2-ylene, prop-1,3-ylene, prop-2,2-ylene, but-1,1-ylene, but-1,2-ylene, but-1,3-ylene, but-1,4-ylene, but-2,2-ylene, 2-methylprop-1,3-ylene, pent-1,1-ylene, pent-1,2-ylene, pent-1,3-ylene, pent-1,4-ylene, pent-1,5-ylene, pent-2,2-ylene, pent-2,3-ylene, pent-2,4-ylene, pent-3,3-ylene, 1-methylbut-1,4-ylene, 2-methylbut-1,4-ylene, hex-1,6-ylene, dodec-1,12-ylene etc., preferably having—unless stated otherwise—1 to 32, in particular 1 to 18 and particularly preferably 1 to 12, carbon atoms.

The terms "alkenylene" and "alkynylene" include straight-chain or branched mono- or poly-, preferably di- or tri-, unsaturated alkylene groups, such as ethenylene, preferably having—unless stated otherwise—2 to 32, in particular 2 to 18 and particularly preferably 2 to 12, carbon atoms.

The term "cycloalkylene" includes divalent cycloalkyl radicals, such as cyclohex-1,4-ylene.

The term "arylene" includes divalent aryl radicals, such as phen-1,4-ylene or diphen-4,4'-ylene.

The term "halogen" includes a fluorine, chlorine, bromine or iodine atom and in particular a fluorine or chlorine atom.

Acyl means —COR, in which R may be alkyl or aryl. Particular mention may be made of acetyl and benzoyl.

Acyloxy means —OCOR in which R may be alkyl or aryl. Particular mention may be made of acetyloxy and benzoyloxy.

Alkoxycarbonyl means —COOalkyl, such as CO—OCH$_3$, CO—OC$_2$H5, CO—OCH$_2$—C$_2$H$_5$, CO—OCH(CH$_3$)$_2$, n-butoxycarbonyl, CO—OCH(CH$_3$)—C$_2$H$_5$, CO—OCH$_2$—CH(CH$_3$)$_2$, CO—OC(CH$_3$)$_3$, in particular CO—OCH$_3$, CO—OC$_2$H5, CO—OCH(CH$_3$)$_2$ or CO—OCH$_2$—CH(CH$_3$)$_2$.

Amino means NH$_2$ and mono- or disubstituted NH(R) or N(R)$_2$. In this connection, R is preferably alkyl and/or acyl.

Substituted radicals, in particular alkyl, alkenyl, alkynyl, cycloalkyl, aryl, aralkyl, alkylene, alkenylene and alkynylene, are preferably mono-, di- or trisubstituted.

Interrupted radicals, in particular alkylene, alkenylene and alkynylene, are preferably interrupted once, twice or three times.

The present invention will now be illustrated by reference to the examples below.

EXAMPLES

Syntheses

Example 1

Preparation of Polymers of Type B a) Adduct of methylamine and ethyl acrylate (compound of the formula XVI where $R^{25(26)}$=—CH$_3$; $R^{53}$, $R^{54}$=H; Z=—CH$_2$CH$_3$)

0.3 mol of methylamine is introduced into 0.6 mol of ethyl acrylate. The resulting adduct is mixed with equal parts by weight of ethanol.

The following adducts b) and c) can be prepared in an analogous manner to the adduct described in a):

b) adduct of methylamine and ethyl methacrylate (compound of the formula XVI where $R^{25(26)}$=—CH$_3$; $R^{53}$, $R^{54}$=—CH$_3$; Z=—CH$_2$CH$_3$)

c) adduct of ethylamine and ethyl acrylate (compound of the formula XVI where $R^{25(26)}$=—CH$_2$CH$_3$; $R^{53}$, $R^{54}$=H; Z=—CH$_2$CH$_3$)

d) quaternized adduct of methylamine and ethyl acrylate (compound of the formula XVII where $R^{25}$, $R^{26}$=—CH$_3$; $R^{53}$, $R^{54}$=H; Z=—CH$_2$CH$_3$; counterion: methylsulfate)

0.3 mol of the quaternizing agent dimethyl sulfate is added to the adduct resulting according to reaction a). After a reaction time of 3 h at room temperature, the reaction mixture is taken up in ethanol.

The following quaternized adducts e) and f) can be prepared in an analogous manner to reaction d) from the adducts with dimethyl sulfate or methyl chloride resulting according to reaction b) or c), respectively:

e) quaternized adduct of methylamine and ethyl methacrylate (compound of the formula XVII where $R^{25}$, $R^{26}$=—CH$_3$; $R^{53}$, $R^{54}$=—CH$_3$; Z=—CH$_2$CH$_3$; counterion: methylsulfate)

f) quaternized adduct of ethylamine and ethyl acrylate (compound of the formula XVII where $R^{25}$=CH$_2$CH$_3$, $R^{26}$=—CH$_3$; $R^{53}$, $R^{54}$=H; Z=—CH$_2$CH$_3$; counterion: chloride)

g) quaternized polyamidoamine of quaternized methylamine/ethyl acrylate adduct and 1,6-diaminohexane (polymer with structural units of the formula VIIB, in which $R^{25}$, $R^{26}$=—$CH_3$; $R^{42}$=—$(CH_2)_6$—; $R^{53}$, $R^{54}$=H; counterion: methylsulfate)

The quaternized adduct of methylamine and ethyl acrylate resulting according to d) is treated with 0.3 mol of 1,6-diaminohexane [CAS No.: 124-09-4]. The reaction mixture is firstly heated to 80° C. and then to 120° C. When the reaction is complete, the reaction mixture is diluted with 1 l of water and ultrafiltered using an ultrafiltration unit (Miniset from PALL) over a 5 kD membrane (Open Channel Omega). The polymer is isolated by freeze-drying (automatic plant gamma 2-Christ).

The following quaternized polyamidoamines h) and i) can be prepared in analogous manner from the quaternized adducts of methylamine and ethyl methacrylate or ethylamine and ethyl acrylate according to e) and f) and 1,6-diaminohexane or 1,12-diaminododecane [CAS No.: 2783-17-7] respectively:

h) quaternized polyamidoamine of quaternized methylamine/ethyl methacrylate adduct and 1,6-diaminohexane (polymer with structural units of formula VIIB, in which $R^{25}$, $R^{26}$=—$CH_3$; $R^{42}$—$(CH_2)_6$—; $R^{53}$, $R^{54}$=—$CH_3$; counterion: methylsulfate)

i) quaternized polyamidoamine of quaternized ethylamine/ethyl acrylate adduct and 1,12-diaminododecane (polymer with structural units of formula VIIB, in which $R^{25}$=—$CH_2CH_3$ and $R^{26}$=—$CH_3$; $R^{42}$=—$(CH_2)_{12}$—; $R^{53}$, $R^{54}$=H; counterion: chloride)

The polymers g), h) and i) of type B are thus prepared via the diester synthesis.

The following further polymers j), k), l), m) and n) of type B are prepared via the diacrylate synthesis:

j) quaternized polyamidoamine of quaternized methylamine/methylenebisacrylamide adduct (polymer with structural units of the formula VIIB, in which $R^{25}$, $R^{26}$=—$CH_3$; $R^{42}$=—$CH_2$—; $R^{53}$, $R^{54}$=—H; counterion: methylsulfate)

0.1 mol of methylenebisacrylamide is slurried in aqueous alcohol with stirring, and 0.05 mol of methylamine is added. The mixture is stirred for 24 hours at room temperature and for a further 48 hours at 30° C. The resulting polymer is then isolated, and three times the amount of methanol is added. Methyl sulfate is then added dropwise in slight excess until a clear solution is present. The temperature is then increased to 60° C. and the mixture is afterstirred. The solvent is stripped off under reduced pressure, and the residue is taken up in water and dialyzed.

The following quaternized polyamidoamines k), l), m) and n) can be prepared in an analogous manner from ethylenebisacrylamide or methylenebisacrylamide and methylamine, octylamine, benzylamine or oleylamine, and methyl chloride or dimethyl sulfate:

k) quaternized polyamidoamine of quaternized methylamine/ethylenebisacrylamide adduct (polymer with structural units of the formula VIIB, in which $R^{25}$, $R^{26}$=—$CH_3$; $R^{42}$=—$(CH_2)_2$—; $R^{53}$, $R^{54}$=—H; counterion: chloride)

l) quaternized polyamidoamine of quaternized octylamine/methylenebisacrylamide adduct (polymer with structural units of the formula VIIB, in which $R^{25}$=—$CH_3$, $R^{26}$=-octyl; $R^{42}$=—$CH_2$—; $R^{53}$, $R^{54}$=—H; counterion: methylsulfate)

m) quaternized polyamidoamine of quaternized benzylamine/methylenebisacrylamide adduct (polymer with structural units of the formula VIIB, in which $R^{25}$=—$CH_3$, $R^{26}$=-benzyl; $R^{42}$=—$CH_2$—; $R^{53}$, $R^{54}$=—H; counterion: methylsulfate)

n) quaternized polyamidoamine of quaternized octylamine/methylenebisacrylamide adduct (polymer with structural units of the formula VIIB, in which $R^{25}$=—$CH_3$, $R^{26}$=-oleyl; $R^{42}$=—$CH_2$—; $R^{53}$, $R^{54}$=—H; counterion: methylsulfate)

Example 2

Preparation of Polymers of Type C

The preparation takes place in accordance with the diester or diacrylate synthesis described in example 1. Instead of the primary amine, i.e. methylamine or ethylamine, the diamines 1,6-diaminohexane and 1,12-diaminododecane are used.

The following polymers a), b) and c) of type C are prepared via the diester synthesis:

a) quaternized polyamidoamine of quaternized 1,2-diethylamine/ethyl acrylate adduct and 1,6-diaminohexane (polymer with structural units of the formula VIIC, in which $R^{12}$=—$(CH_2)_6$—; $R^{27}$, $R^{28}$, $R^{29}$, $R^{210}$=—$CH_3$; $R^{43}$=—$(CH_2)_2$—; $R^{55}$, $R^{56}$=H; counterion: methylsulfate)

b) quaternized polyamidoamine of quaternized 1,6-diaminohexane/ethyl methacrylate adduct and 1,6-diaminohexane (polymer with structural units of the formula VIIC, in which $R^{12}$=—$(CH_2)_6$—; $R^{27}$, $R^{28}$, $R^{29}$, $R^{210}$=—$CH_3$; $R^{43}$=—$(CH_2)_6$—; $R^{55}$, $R^{56}$=—$CH_3$; counterion: methylsulfate)

c) quaternized polyamidoamine of quaternized 1,6-diaminohexane/ethyl acrylate adduct and 1,12-diaminododecane (polymer with structural units of the formula VIIC, in which $R^{12}$=—$(CH_2)_{12}$—; $R^{27}$, $R^{28}$, $R^{29}$, $R^{210}$=—$CH_3$; $R^{43}$=—$(CH_2)_6$—; $R^{55}$, $R^{56}$=H; counterion: methylsulfate)

The following further polymers d), e) and f) of type C are prepared via the diacrylate synthesis:

d) quaternized polyamidoamine of quaternized 1,6-diaminohexane/methylenebisacrylamide adduct (polymer with structural units of the formula VIIC, in which $R^{12}$=—$(CH_2)_6$—; $R^{27}$, $R^{28}$, $R^{29}$, $R^{210}$=—$CH_3$; $R^{43}$=—$CH_2$—; $R^{55}$, $R^{56}$=H; counterion: methylsulfate)

e) quaternized polyamidoamine of quaternized 1,6-diaminohexane/methylenebisacrylamide adduct (polymer with structural units of the formula VIIC, in which $R^{12}$=—$(CH_2)_6$—; $R^{27}$, $R^{28}$, $R^{29}$, $R^{210}$=—$CH_3$; $R^{43}$=—$CH_2$—; $R^{55}$, $R^{56}$=H; counterion: chloride)

f) quaternized polyamidoamine of quaternized 1,6-diaminohexane/ethylenebisacrylamide adduct (polymer with structural units of the formula VIIC, in which $R^{12}$=—$(CH_2)_6$—; $R^{27}$, $R^{28}$, $R^{29}$, $R^{210}$=—$CH_3$; $R^{43}$=—$(CH_2)_2$—; $R^{51}$, $R^{52}$=H; counterion: methylsulfate)

Example 3

Preparation of Polymers of Type A a) 1,2-Bis(chloroacetamido)ethane (compound of the formula XI where $R^{41}$=eth-1,2-ylene; $R^{71}$, $R^{72}$=H; X=Cl; a1, a2, c=1)

The preparation took place in accordance with B. B. Corson et al., Org. Syntheses, Coll. Vol. I (1941), 179 and H. Schindlbauer and H. Gusbeth, Makromol. Chem. 185, 239–247 (1984).

Further chloracetamido-disubstituted alkanes of the formula XI can be prepared in an analogous manner, for example 1,3-bis(chloroacetamido)propane from ethyl chloroacetate and 1,3-propanediamine.
  b) Quaternized polyamidamine of 1,2-bis(chloroacetamido)propane and N,N,N',N'-tetramethyl-1,12-diaminohexane (polymer with structural units of the formula VIIA, where $R^{11}$=—$(CH_2)_6$—; $R^{21}$, $R^{22}$, $R^{23}$, $R^{24}$=—$CH_3$; $R^{41}$=—$(CH_2)_3$—; $R^{71}$, $R^{72}$H; a1, a2=1; counterion: chloride)

0.3 mol of 1,2-bis(chloroacetamido)proane are dissolved in a solvent mixture of 4/1 parts by volume of DMF/MeOH in a weight ratio of 1:1. 0.3 mol of N,N,N',N'-tetramethyl-1,12-diaminohexane (prepared in accordance with Leuckart-Wallach: H. G. O. Becker et al., Organikum—Organisch-Chemisches Grundpraktikum, 18th edition, Deutscher Verlag der Wissenschaften, Berlin 1990, p. 491) are added dropwise at room temperature such that the reaction temperature (about 20–30° C.) remains essentially constant. When the feed is complete, the reaction temperature is further maintained for about 1 hour and then increased to 70° C. and held there until further conversion can no longer be measured. When the reaction is finished, the reaction mixture is diluted with 1 l of water and subjected to ultrafiltration using an ultrafiltration plant (Minisette from PALL) over a 5 kD membrane (Open Channel Omega). The polymer is isolated by freeze-drying (automatic plant gamma 2-christ).

The following polymers were prepared in an anlagous manner:
  c) Quaternized polyamidoamine of 1,3-bis(chloroacetamido)propane and N,N,N',N'-tetramethyl-1,6-diaminododecane [CAS number: 124-09-4] (polymer with structural units of the formula VIIA, where $R^{11}$=—$(CH_2)_{12}$—; $R^{21}$, $R^{22}$, $R^{23}$, $R^{24}$=—$CH_3$; $R^{41}$=—$(CH_2)_3$—; $R^{71}$, $R^{72}$=H; a1, a2=1; counterion: chloride)
  d) Quaternized polyamidoamine of 1,3-bis(chloroacetamido)propane and a ?:? mixture of N,N,N',N'-tetramethyl-1,6-diaminododecane [CAS number: 124-09-4] and N,N,N',N'-tetramethyl-1,6-diaminododecane [CAS number: 124-09-4] (polymer with structural units of the formula VIIA, where $R^{11}$=—$(CH_2)_6$—$(CH_2)_{12}$—; $R^{21}$, $R^{22}$, $R^{23}$, $R^{24}$=—$CH_3$; $R^{41}$=—$(CH_2)_3$—; $R^{71}$, $R^{72}$=H; a1, a2=1; counterion: chloride)
  e) Quaternized polyamidoamine of 1,3-bis(chloroacetamido)ethane and N,N,N',N'-tetramethyl-1,6-diaminohexane [CAS number: 124-09-4] (polymer with structural units of the formula VIIA, where $R^{11}$=—$(CH_2)_6$—; $R^{21}$, $R^{22}$, $R^{23}$, $R^{24}$=—$CH_3$; $R^{41}$=—$(CH_2)_2$—; $R^{71}$, $R^{72}$=H; a1, a2=1; counterion: chloride)
  e) Quaternized polyamidoamine of 1,3-bis(chloroacetamido)butane and N,N,N',N'-tetramethyl-1,6-diaminohexane [CAS number: 124-09-4] (polymer with structural units of the formula VIIA, where $R^{11}$=—$(CH_2)_6$—; $R^{21}$, $R^{22}$, $R^{23}$, $R^{24}$=—$CH_3$; $R^{41}$=—$(CH_2)_4$—; $R^{71}$, $R^{72}$=H; a1, a2=1; counterion: chloride)

Biological Effect

Example 4

Assessment of the Microbiostatic or Microbiocidal Effect of Quaternized Polymers of Type A and B The generally known method of microtiter screening was used (trypton-soya-agar and sabouraud-dextrose-agar; control: distilled water; incubation: at least 5 days at 25° C. for SAB plates or at least 3 days at 30° C. for TSA plates), in order to evaluate the microstatic or microbiocidal effect of the given polymers on a series of microbes by reference to the ascertained MIC (minimum inhibitory concentration, in each case based on the concentration of polyamidoamine). Cultures from the second pass, and 24-hour and 5-day nutrient cultures for bacteria and *C. albicans*, and a spore suspension of a 7 day-old *Aspergillus niger* culture were used.

a) Bacteria:
  *Pseudomonas aeruginosa* (Pa), *Staphylococcus aureus* (Sa), *Bacillus subtilis* (Bs), *Escherichia coli* (Ec);
b) Yeasts:
  *Saccharomyces cerevisiae* (Sc), *Candida albicans* (Ca);
c) Fungi:
  *Aspergillus niger* (An).

The polyamidoamines of type A described in examples 3b, 3c, 3d, 3e, and the polyamidoamine of type B described in example 1n display not only a bactericidal effect (MIC for gram-negative bacteria in the range from about 10 to 500 ppm, for gram-positive in the range from about 100 to 1000 ppm), but they are also effective against yeasts and fungi (about 250 to 2000 ppm).

We claim:
1. A quaternized polyamidoamine comprising at least one structural unit of the formula VIIBC

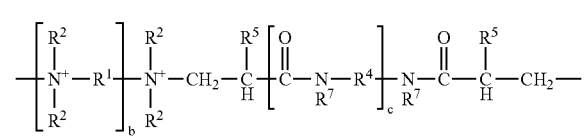

in which
  $R^1$, $R^2$, $R^4$, independently of one another, are straight-chain or branched organic radicals optionally containing heteroatoms;
  $R^5$ is hydrogen or alkyl,
  $R^7$ is hydrogen or alkyl or two radicals $R^7$ together form a radical having a meaning given for $R^4$,
  b is an integer from 0 to 50, and
  c is an integer from 1 to 50.
2. A quaternized polyamidoamine as claimed in claim 1, wherein
  $R^1$ is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene,
  $R^2$ is straight-chain or branched alkyl, alkenyl or aralkyl which may be substituted by groups chosen independently of one another from alkyl, halogen, cyano, hydroxyl and alkoxy, and may be interrupted by one or more groups chosen independently of one another from O, S, CO, NH, and N(alkyl), and
  $R^4$ is straight-chain or branched alkylene, alkenylene or alkynylene which may be substituted by one or more groups chosen, independently of one another, from halogen, cyano, hydroxyl, alkoxy, thioalkyl, acyl, acyloxy, alkoxycarbonyl, carboxy, amino, and may be interrupted by one or more groups chosen, independently of one another, from O, S, CO, NH, N(alkyl), arylene and cycloalkylene.

3. A quaternized polyamidoamine as claimed in claim 1, having repeat units of the formula VIIIB

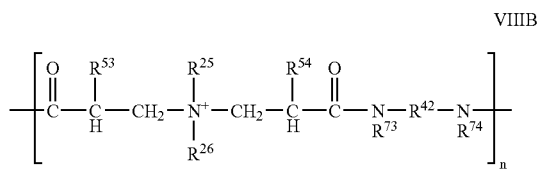

VIIIB in which $R^{25}$, $R^{26}$, independently of one another, are straight-chain or branched alkyl, alkenyl or aralkyl which may be substituted by one or more groups chosen independently of one another from alkyl, halogen, cyano, hydroxyl and alkoxy, $R^{42}$ is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^{53}$, $R^{54}$, independently of one another, are hydrogen or alkyl, $R^{73}$, $R^{74}$ are hydrogen or alkyl or the two radicals together form a radical having a meaning given for $R^{42}$, and n is an integer from 3 to 200.

4. A quaternized polyamidoamine as claimed in claim 3, wherein $R^{25}$, $R^{26}$ are methyl, ethyl, octyl, oleyl or benyzl, $R^{42}$ is $C_{1-18}$-alkylene, $R^{53}$, $R^{54}$ is hydrogen or methyl, $R^{73}$, $R^{74}$ are hydrogen, and n is an integer from 10 to 150.

5. A quaternized polyamidoamine as claimed in claim 1, having repeat units of the formula VIIIC

VIIIC

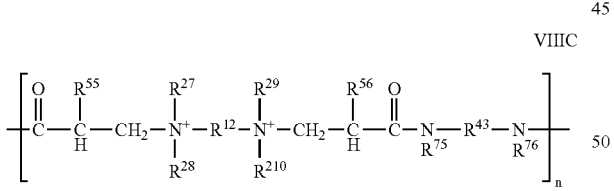

in which $R^{12}$ is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^{27}$, $R^{28}$, $R^{29}$, $R^{210}$, independently of one another, are straight-chain or branched alkyl, alkenyl or aralkyl which may be substituted by one or more groups chosen independently of one another from alkyl, halogen, cyano, hydroxyl and alkoxy, $R^{43}$ is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^{55}$, $R^{56}$, independently of one another, are hydrogen or alkyl, $R^{75}$, $R^{76}$ are hydrogen or alkyl or the two radicals together form a radical having a meaning given for $R^{43}$, and n is an integer from 3 to 200.

6. A quaternized polyamidoamine as claimed in claim 5, wherein $R^{12}$ is straight-chain or branched $C_{1-32}$-alkylene, $R^{27}$, $R^{28}$, $R^{29}$, $R^{210}$ are methyl, ethyl, octyl, oleyl or benzyl, $R^{43}$ is $C_{1-18}$-alkylene, $R^{55}$, $R^{56}$ are hydrogen or methyl, $R^{75}$, $R^{76}$ are hydrogen, and n is an integer from 10 to 150.

7. A process for the preparation of a quaternized polyamidoamine of the formula VIIIB as claimed in claim 3 by a) Michael addition of a primary amine of the formula XIV $$H_2N-R^{25(26)} \quad \text{XIV}$$

in which $R^{25}$, $R^{26}$ independently of one another, are straight-chain or branched alkyl, alkenyl or aralkyl which may be substituted by one or more groups chosen independently of one another from alkyl, halogen, cyano, hydroxyl and alkoxy, with at least two equivalents of an α,β-unsaturated carboxylic acid or of a derivative thereof of the formula XV

XV

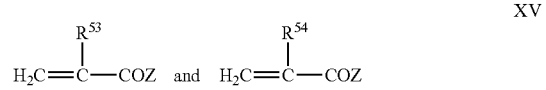

in which $R^{53}$, $R^{54}$ independently of one another, are hydrogen or alkyl, and Z is hydroxyl or alkoxy;

b) optional quaternization of the adduct of the formula XVI resulting in stage a)

XVI

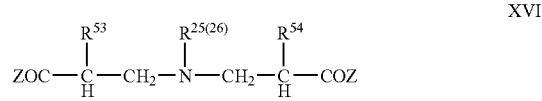

in which $R^{25}$, $R^{26}$, $R^{53}$, $R^{54}$, Z have the above meanings, c) reaction of the adduct of the formula XV resulting in stage a) or of the quaternization product of the formula XVII resulting in stage b)

XVII

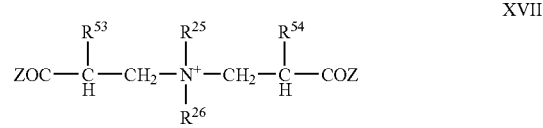

in which $R^{25}$, $R^{26}$, $R^{53}$, $R^{54}$, Z have the above meanings, with a diamine of the formula XVIII $$(R^{73})HN-R^{42}-NH(R^{74}) \qquad XVIII$$

in which $R^{42}$ is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^{73}$, $R^{74}$ are hydrogen or alkyl or the two radicals together form a radical having a meaning given for $R^{42}$, d) optional quaternization of the polyamidoamine of the formula XIX resulting in stage c)

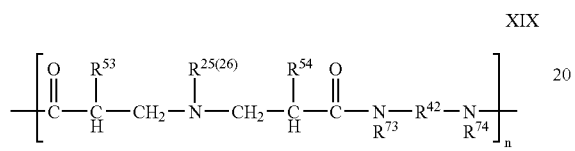

XIX in which $R^{25}$, $R^{26}$, $R^{42}$, $R^{53}$, $R^{54}$, $R^{73}$, $R^{74}$ have the above meanings.

8. A process for the preparation of a quaternized polyamidoamine of the formula VIIIB as claimed in claim 3 by
a) Michael addition of a compound of the formula XIV $$H_2N-R^{25(26)} \qquad XIV$$

in which $R^{25}$, $R^{26}$ independently of one another, are straight-chain or branched alkyl, alkenyl or aralkyl which may be substituted by one or more groups chosen independently of one another from alkyl, halogen, cyano, hydroxyl and alkoxy, with at least one equivalent of an α,β-unsaturated carboxylic acid diamide of the formula XX

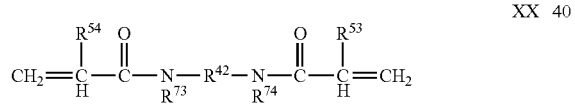

XX in which $R^{42}$ is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^{53}$, $R^{54}$ independently of one another, are hydrogen or alkyl, $R^{73}$, $R^{74}$ are hydrogen or alkyl or the two radicals together form a radical having a meaning given for $R^{42}$, b) quaternization of the polyamidoamine of the formula XIX resulting in stage a)

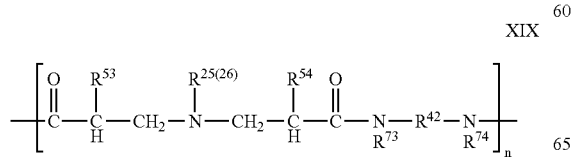

XIX where $R^{25}$, $R^{26}$, $R^{42}$, $R^{53}$, $R^{54}$, $R^{73}$, $R^{74}$ have the above meanings.

9. A process for the preparation of a quaternized polyamidoamine of the formula VIIIC as claimed in claim 5 in an analogous manner via the process stages to
a) Michael addition of a primary amine of the formula XIV $$H_2N-R^{25(26)} \qquad XIV$$

in which $R^{25}$, $R^{26}$ independently of one another, are straight-chain or branched alkyl, alkenyl or aralkyl which may be substituted by one or more groups chosen independently of one another from alkyl, halogen, cyano, hydroxyl and alkoxy, with at least two equivalents of an α,β-unsaturated carboxylic acid or of a derivative thereof of the formula XV

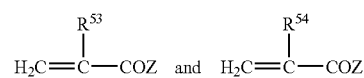

XV in which $R^{53}$, $R^{54}$ independently of one another, are hydrogen or alkyl, and Z is hydroxyl or alkoxy;

b) optional quaternization of the adduct of the formula XVI resulting in stage a)

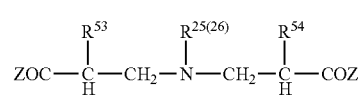

XVI in which $R^{25}$, $R^{26}$, $R^{53}$, $R^{54}$, Z have the above meanings, c) reaction of the adduct of the formula XV resulting in stage a) or of the quaternization product of the formula XVII resulting in stage b)

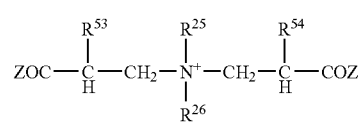

XVII in which $R^{25}$, $R^{26}$, $R^{53}$, $R^{54}$, Z have the above meanings, with a diamine of the formula XVIII $$(R^{73})HN-R^{42}-NH(R^{74}) \qquad XVIII$$

in which $R^{42}$ is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^{73}$, $R^{74}$ are hydrogen or alkyl or the two radicals together form a radical having a meaning given for $R^{42}$, d) optional quaternization of the polyamidoamine of the formula XIX resulting in stage c)

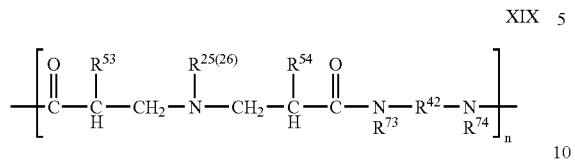

in which $R^{25}$, $R^{26}$, $R^{42}$, $R^{53}$, $R^{54}$, $R^{73}$, $R^{74}$ have the above meanings, where, in stage a), instead of the primary amine of the formula XIII, a primary or secondary diamine of the formula XXI

is used, in which $R^{12}$, is straight-chain or branched alkylene, alkenylene or alkynylene which may be substituted by one or more groups chosen independently of one another from halogen, cyano, hydroxyl, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^{27}$, $R^{28}$, $R^{29}$, $R^{210}$ independently of one another, are straight-chain or branched alkyl, alkenyl or aralkyl which may be substituted by one or more groups chosen independently of one another from alkyl, halogen, cyano, hydroxyl and alkoxy.

10. A process as claimed in claim 7, wherein methyl chloride, dimethyl sulfate, diethyl sulfate or ethylene oxide is used as quaternizing agent.

11. A composition based on at least one quaternized polyamidoamine as claimed in claim 1, optionally with further active ingredients and/or auxiliaries.

12. A cosmetic composition, a pharmaceutical composition, a crop protection composition or a textile dye, comprising:
at least one quaternized polyamidoamine as claimed in claim 1.

13. A method of inhibiting growth and/or replication of an organism or killing of an organism, comprising:
contacting a fluid or a surface of an article with at least one quaternized polyamidoamine as biostatic or biocide,
wherein the polyamidoamine has structural units which are selected from the group consisting of structural units i), ii) and iii):
i) structural units of the formula I

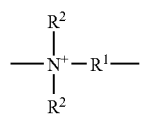

ii) structural units of the formula II

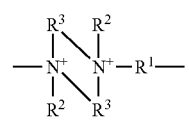

iii) structural units of the formula III

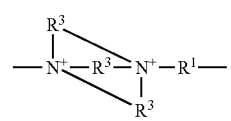

in which $R^1$ is straight-chain or branched alkylene, alkenylene or alkynylene, which may be substituted by one or more groups chosen independently of one another from halogen, cyano, hydroxy, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, $R^2$ is straight-chain or branched alkyl, alkenyl or aralkyl, which may be substituted by groups chosen independently of one another from alkyl, halogen, cyano, hydroxy and alkoxy, and may be interrupted by one or more groups chosen independently of one another from O, S, CO, NH, and N(alkyl), $R^3$ is straight-chain or branched alkylene, alkenylene or alkynylene, which may be substituted by one or more groups chosen independently of one another from halogen, cyano, hydroxy and alkoxy, and may be interrupted by one or more groups chosen independently of one another from O, S, CO, NH, and N(alkyl), and at least one of the radicals $R^1$, $R^2$ and $R^3$ has at least one amide bond.

14. The method as claimed in claim 13, wherein the organisms are bacteria, fungi, yeasts or combinations thereof.

15. The method as claimed in claim 13, wherein the quaternized polyamidoamine has at least one structural unit of the formula IV

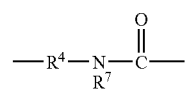

in which $R^4$ is straight-chain or branched alkylene, alkenylene or alkynylene, which may be substituted by one or more groups chosen independently of one another from halogen, cyano, hydroxy, alkoxy, thioalkyl, acyl, acyloxy, alkoxycarbonyl, carboxy, amino, and may be interrupted by one or more groups chosen independently of one another from O, S, CO, NH, N(alkyl), arylene and cycloalkylene, and $R^7$ is hydrogen or alkyl, or two radicals $R^7$ together form a radical with a meaning given for $R^4$.

16. The method as claimed in claim 15, wherein $R^4$ is $C_{1-18}$-alkylene and $R^7$ is hydrogen.

17. The method as claimed in claim 13, wherein the polyamidoamine has at least one structural unit of the formula VIIA

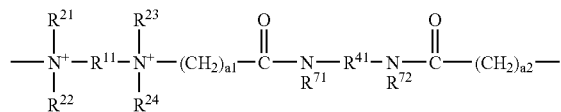

VIIA in which $R^{11}$ is straight-chain or branched $C_{1-32}$-alkylene, $R^{21}$, $R^{22}$, $R^{23}$, $R^{24}$, independently of one another, are $C_{1-8}$-alkyl, $C_{2-32}$-alkenyl or benzyl, $R^{41}$ is $C_{1-18}$-alkylene, $R^{71}$, $R^{72}$, independently of one another, are hydrogen or together are eth-1,2-ylene, and a1, a2, independently of one another, are an integer from 1 to 30.

18. The method as claimed in claim 13, wherein the biostatic or biocide comprises at least one polyamidoamine comprising at least one structural unit of the formula VIIBC

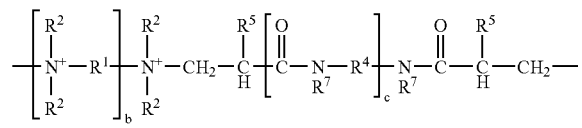

in which $R^1$, $R^2$, $R^4$, independently of one another, are straight-chain or branched organic radicals optionally containing heteroatoms;

$R^5$ is hydrogen or alkyl, $R^7$ is hydrogen or alkyl or two radicals $R^7$ together form a radical having a meaning given for $R^4$, b is an integer from 0 to 50, and c is an integer from 1 to 50.

19. A biocidal composition, comprising:

at least one quaternized polyamidoamine as claimed in claim 1, optionally with further active ingredients and/or auxiliaries.

20. A composition as claimed in claim 19, which comprises, as further active ingredient, an ionone with repeat units of the formula IXA

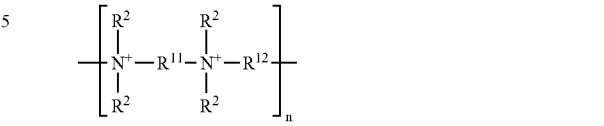

IXA in which $R^{11}$ is $C_{1-8}$-alkylene, $R^{12}$ is $C_{8-24}$-alkylene, $R^3$ is $C_{1-3}$-alkyl and n is an integer from 10 to 300.

21. A composition as claimed in claim 20, wherein $R^1$ is —$(CH_2)_6$—, $R^2$ is —$(CH_2)_{12}$—, $R^3$ is —$CH_3$— and n is an integer from 10 to 150.

22. A process as claimed in claim 8, wherein methyl chloride, dimethyl sulfate, diethyl sulfate or ethylene oxide is used as quaternizing agent.

23. A process as claimed in claim 9, wherein methyl chloride, dimethyl sulfate, diethyl sulfate or ethylene oxide is used as quaternizing agent.

24. A biocidal composition based on at least one quaternized polyamidoamine as claimed in claim 13, optionally with further active ingredients and/or auxiliaries.

25. A composition as claimed in claim 24, which comprises, as further active ingredient, an ionone with repeat units of the formula IXA

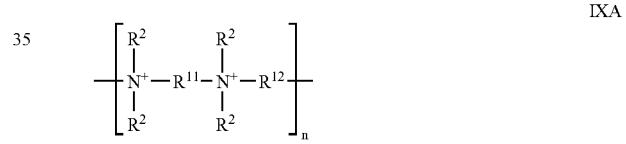

IXA in which $R^{11}$ is $C_{1-8}$-alkylene, $R^{12}$ is $C_{8-24}$-alkylene, $R^3$ is $C_{1-3}$-alkyl and n is an integer from 10 to 300.

26. A composition as claimed in claim 19, wherein $R^1$ is —$(CH_2)_6$—, $R^2$ is —$(CH_2)_{12}$—, $R^3$ is —$CH_3$— and n is an integer from 10 to 150.

* * * * *